United States Patent [19]

Laviron et al.

[11] Patent Number: 5,202,509
[45] Date of Patent: Apr. 13, 1993

[54] CATALYSTS FOR LIQUID PHASE FLUORINATION

[75] Inventors: Charles Laviron, Lyon; Andre Lantz, Vernaison, both of France

[73] Assignee: Societe Atochem, Puteaux, France

[21] Appl. No.: 890,343

[22] Filed: May 20, 1992

Related U.S. Application Data

[63] Continuation of Ser. No. 576,875, Sep. 4, 1990, abandoned.

[30] Foreign Application Priority Data

Sep. 1, 1989 [FR] France .................................. 89 11490

[51] Int. Cl.$^5$ ............................................. C07C 17/08
[52] U.S. Cl. ..................................... 570/167; 570/168
[58] Field of Search .................................. 570/187, 188

[56] References Cited

U.S. PATENT DOCUMENTS 3,324,126  6/1967  Mertes et al. .
4,374,289  2/1983  Van Der Puy et al. .
4,623,491  11/1986  Siegemund et al. .
4,792,643  12/1988  Sobolev .................................. 570/168

FOREIGN PATENT DOCUMENTS 1041026  10/1958  Fed. Rep. of Germany ...... 570/167
2388785  12/1978  France .................................. 570/188
1178284   1/1970  United Kingdom ................ 570/188

OTHER PUBLICATIONS

"Methoden Der Organischen Chemie" Houben-Weyl, vol. V/3, 1962, p. 126 with English translation.

*Primary Examiner*—Alan Siegel
*Attorney, Agent, or Firm*—Morgan & Finnegan

[57] ABSTRACT

The catalysts according to the invention are mixtures of an antimony trihalide and of a titanium tetrahalide.

These catalysts can be used for the liquid phase fluorination of halogenated aliphatic hydrocarbons, especially that of chlorinated ethane and ethylene derivatives.

14 Claims, No Drawings

CATALYSTS FOR LIQUID PHASE FLUORINATION

This is a continuation of co-pending application Ser. No. 07/576,875, filed on Sep. 4, 1990, now abandoned.

FIELD OF THE INVENTION

The present invention relates to catalysts consisting of mixtures of trivalent antimony and tetravalent titanium halides and their use for liquid phase fluorination with anhydrous hydrofluoric acid of halogenated, especially chlorinated, aliphatic derivatives.

BACKGROUND OF THE INVENTION

Liquid phase fluorination of aliphatic chlorinated derivatives, that is to say the chlorine-fluorine exchange with anhydrous hydrofluoric acid in liquid phase is a known reaction. The most important chlorofluorocarbons, that is to say $CFCl_3$, $CF_2Cl_2$, $CHF_2Cl$, and $C_2Cl_3F_3$, can thus be obtained according to a process of this kind by chlorine-fluorine exchange, starting with $CCl_4$, $CHCl_3$, and $C_2Cl_6$ respectively (J. M. Hamilton, "The Organic Fluorochemicals Industry" in the work Advances in Fluorine Chemistry, vol. 3, 1963, pp. 146–150).

The aliphatic fluoro or chlorofluoro derivatives containing at least two carbon atoms and containing at least one hydrogen atom can be obtained according to the same fluorination process from the corresponding chloro derivatives, but they can also generally be obtained from chloroolefins by reaction with hydrofluoric acid according to a reaction whose first stage is an addition of HF to the double bond. Thus, for example, $CF_3CH_3$ can be obtained either by fluorination of $CCl_3CH_3$ or by fluorination of $CCl_2=CH_2$ (E. T. McBee, et al., I.E.C., 1947, pp. 409–412). Similarly, $CF_3CH_2Cl$ can be obtained by fluorination of $CCl_3CH_2Cl$ or of $CCl_2=CHCl$ (A. K. Barbour, et al., "The Preparation of Organic Fluorine Compounds by Halogen Exchange" in the work Advances in Fluorine Chemistry, vol. 3, 1963, pp. 197–198).

In some cases, with highly reactive chloro derivatives, it is possible to effect these fluorinations merely by heating the chloro derivative with hydrofluoric acid in the absence of catalyst. Thus, it is known that methylchloroform $CCl_3CH_3$ can be converted into $CF_3CH_3$ by reaction with anhydrous hydrofluoric acid in liquid phase (E. T. McBee, et al., op.cit.). This reactivity of methylchloroform is, however, quite exceptional and, generally speaking, the reaction of HF in the absence of catalyst does not allow the chlorine-fluorine exchange to be effected or permits only a single chlorine atom to be replaced, and even this at very high temperatures. In practice, liquid phase fluorinations are carried out in the presence of a fluorination catalyst. Various catalysts have been proposed, but the most effective ones have been found among pentavalent antimony halides or mixtures of pentavalent and trivalent antimony halides (Houben-Weyl, Vol. V/3, 1962, p. 126). On an industrial scale, antimony pentachloride $SbCl_5$ or a mixture of antimony trichloride $SbCl_3$ and chlorine are generally employed, and these, on reacting with hydrofluoric acid, yield mixed chlorofluorides such as $SbF_3Cl_2$ or $SbF_2Cl_3$, which have been found to be particularly effective fluorination catalysts. However, pentavalent antimony chlorofluorides decompose at the temperatures needed for the fluorination and yield trivalent antimony halides and chlorine. Because trivalent antimony halides are practically ineffective in fluorination, catalysts based on antimony 5+ quickly lose their effectiveness and their activity can be maintained only if the antimony is successfully maintained in its 5+ oxidation state. This can be done by reoxidation using chlorine, that is to say by performing the fluorination in the presence of a little chlorine, which enables $Sb^{3+}$ to be continually reoxidized to $Sb^{5+}$ (Houben-Weyl op.cit.). Nevertheless, catalysts containing antimony exhibit a number of disadvantages:

Mixtures of pentavalent antimony halides and of hydrofluoric acid are highly corrosive, especially at high temperature.

Fluorination in the presence of antimony 5+ is in certain cases accompanied by inconvenient side reactions. Thus, in the case of chloro derivatives containing a hydrogen atom, an olefin can be formed by the loss of HCl, and these olefins can give rise to the formation of heavy products (Houben-Weyl, op.cit., pp. 134–135).

The need for the fluorination to be carried out in the presence of chlorine can also give rise to the formation of a number of secondary reactions. This is the case in particular with the fluorination of chlorinated hydrocarbons still containing one or more hydrogen atoms, which can be replaced by chlorine atoms during this fluorination. In the case where the starting material to be fluorinated is an ethylenic derivative there may be competition between an addition of HF or a chlorine addition to the double bond. In the case of trichloroethylene, it is thus possible to obtain $CF_3CH_2Cl$ by HF addition (Houben-Weyl, p. 107) or $CF_2Cl$-$CFCl_2$ by chlorination (Houben-Weyl, p. 134).

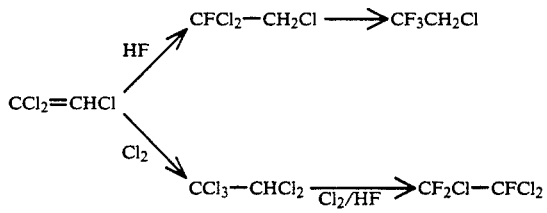

Other catalysts for liquid phase fluorination have been proposed. For example, the compounds $SnCl_4$, $MoCl_5$, $WF_6$, $NbCl_5$, $TaF_5$, $TiCl_4$, $BF_3$, and $CF_3SO_3H$ may be mentioned, but these catalysts are generally much less efficient than antimony 5+. Thus, titanium halides have been proposed for the preparation of chlorofluoro-methane or -ethane compounds by fluorination of the corresponding chlorinated derivatives (U.S. Pat. No. 2,439,299). Titanium tetrachloride can also be employed for the fluorination of chloroolefins such as tri- or tetrachloroethylenes (U.S. Pat. No. 4,374,289 and A. E. Feiring, J. Fluor. Chem. 1979, 13, pp. 7–18), for example:

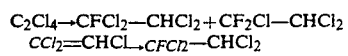

However, this titanium halide is not a very powerful catalyst, because it generally makes it possible to obtain only monofluorinated or difluorinated products.

DETAILED DESCRIPTION OF THE INVENTION

Applicants have found that, while $Ti^{4+}$ and $Sb^{3+}$ halides are relatively inefficient catalysts for liquid phase fluorination, a mixture of the two $Ti^{4+}$ and $Sb^{3+}$ halides is, on the contrary, much more efficient. For example, it permits $CF_3CH_2Cl$ to be prepared from $CCl_3CH_2Cl$ or from $CCl_2=CHCl$ without giving rise to the same disadvantages as the $Sb^{5+}$ halides (the need to employ chlorine to reoxidize antimony $3+$ to antimony $5+$). Other, nonlimiting examples of use of this $Ti^{4+}/Sb^{3+}$ catalyst are the fluorination of methane chloro derivatives such as $CCl_4$, $CHCl_3$ or $CH_2Cl_2$ or of ethane or ethylene chloro derivatives such as $C_2Cl_6$, $CCl_3CHCl_2$, $CCl_3CH_3$, $CCl_2=CCl_2$, $CCl_2=CH_2$, $CHCl_2CH_2Cl$ and $CHCl=CHCl$.

Although the catalyst according to the invention is more particularly intended for fluorinating chloro derivatives, it can also be employed for the fluorination of bromo or iodo derivatives such as, for example, $CBr_4$, $CHBr_3$, $CHBr_2Cl$, $CF_2Br_2$, $CBr_3CH_2Br$ or $CHBr_2-CHBr_2$.

The active form of the catalyst according to the invention is a mixture of $TiF_4$ and of $SbF_3$. It is thus possible to employ such a mixture of fluorides, but it is also possible to employ a mixture of other halides, especially a mixture of the chlorides $TiCl_4$ and $SbCl_3$, which is converted with hydrofluoric acid into $TiF_4$ and $SbF_3$ before or during the fluorination of the halogenated hydrocarbon to be fluorinated.

The proportions of $Ti^{4+}$ and of $Sb^{3+}$ may vary within wide limits, but it is preferred to employ mixtures containing 30 to 90 mol % of $Ti^{4+}$ and 70 to 10 mol % of $Sb^{3+}$ and, more particularly, mixtures in which the molar proportion of $Ti^{4+}$ is comprised between 50 and 90%.

The temperature of fluorination can also vary within wide limits and temperatures between 40° C. and 180° C. are generally employed. The pressure required for the reaction is at least that needed to keep the reaction mixture in liquid phase. It therefore depends essentially on the reaction temperature and can vary within limits which are as wide as 10 to 100 bars.

The reaction may be carried out noncontinuously, in an autoclave. In this case, the catalyst ($TiF_4$—$SbF_3$ mixture or $TiCl_4$—$SbCl_3$ mixture), hydrofluoric acid and the halogenated derivative to be fluorinated are introduced into the autoclave and the mixture is heated to the reaction temperature, preferably with stirring. The reaction pressure is the autogenous pressure in this case.

The reaction can also be carried out continuously. Because the substitution of a chlorine atom by a fluorine atom is accompanied by a lowering of the boiling point, it is possible, for example, to introduce continuously into a reactor containing the catalyst, hydrofluoric acid and the derivative to be fluorinated and to extract continuously a gaseous phase containing the hydrochloric acid formed, the fluoro derivative and optionally hydrofluoric acid. In this case, the reaction can take place at a constant pressure, which must be at least equal to that needed to keep the reaction mixture in liquid phase at the temperature of reaction.

The quantity of catalyst can vary within wide limits. The molar ratio of the catalyst (antimony plus titanium) to the reactant to be fluorinated can thus vary from 0.1 to 0.6, but lesser or greater quantities can also be employed. However, in the case of substrates which are difficult to fluorinate, it is generally preferred to employ quantities corresponding to a molar ratio of 0.2 to 0.4.

The proportion of hydrofluoric acid to be employed depends to a large extent on the nature of the halogenated derivative to be fluorinated and can vary within wide limits. Nevertheless, an excess of HF is generally employed, that is to say an HF/compound to be fluorinated molar ratio of more than 1, it being possible for this ratio to reach very high values, that is to say 5 to 20 or even higher.

EXAMPLES

The following examples illustrate the invention without limiting it. They were carried out in the equipment and according to the procedures which are described below:

EQUIPMENT

An 800-ml autoclave, stirred with a bar magnet and heated by means of oil circulating in a jacket is employed. It is equipped with a temperature tap, pressure measurement and two branches permitting products to be withdrawn either from the gas phase or from the liquid phase.

PROCEDURE

In all cases the reactants, that is to say hydrofluoric acid and the compound to be fluorinated, are introduced into the autoclave containing the catalyst and maintained at the temperature of liquid nitrogen.

The reactor is then heated to the reaction temperature and is maintained at this temperature for a certain time.

At the end of reaction the autoclave is cooled to ambient temperature. It is then decompressed and then purged with a stream of helium through a water scrubber to remove the hydracids and through a drier containing $CaCl_2$. The unabsorbed products are trapped at liquid nitrogen temperature. The content of the trap and optionally that of the autoclave are then analyzed.

EXAMPLE 1

11.6 g of $SbCl_3$ (0.051 moles) and 9.7 g of $TiCl_4$ (0.051 moles) are introduced into the autoclave described above. After cooling with liquid nitrogen, 87.3 g of $CCl_3CH_2Cl$ (0.52 moles) and 101.3 g of HF (5.06 moles) are introduced.

The autoclave is then heated to 150° C. with stirring over two hours and is maintained at this temperature for 3 and a half hours. At the end of reaction the pressure reaches 82 bars. After cooling, the products formed are recovered using the method described above. 60.5 g of product containing 97% of $CF_3CH_2Cl$ and 2% of $CF_2ClCH_2Cl$ are thus obtained, which corresponds to a 95% conversion of $CCl_3CH_2Cl$ into $CF_3CH_2Cl$ and 2% into $CF_2ClCH_2Cl$.

A slightly hygroscopic solid weighing approximately 15.5 g and containing essentially antimony, titanium and fluorine is collected from the autoclave.

EXAMPLE 2

5.7 g (0.025 moles) of $SbCl_3$ and 5 g of $TiCl_4$ (0.026 moles) are introduced into the autoclave.

After cooling, 20 g of HF are introduced and the autoclave is then heated to 50° C. and is maintained at this temperature for one hour. After cooling to ambient temperature, the autoclave is degassed and the excess HF and the HCl formed are removed completely by entrainment with a stream of helium. Approximately 7.5 g of product remain in the autoclave, corresponding in weight to a mixture of $TiF_4$ and $SbF_3$.

40.3 g of $CCl_3CH_2Cl$ (0.24 moles) and 38.8 g of HF (1.94 moles) are then introduced at the temperature of liquid nitrogen.

The autoclave is heated to 150° C. over 2 hours and is maintained at 150° C. for 3 and a half hours. At the end of reaction the pressure has risen to 52 bars. The usual procedure is then followed to recover 27.8 g of products, analyzed as 98.5% of $CF_3CH_2Cl$ and 1% of $CF_2ClCH_2Cl$.

EXAMPLES 3, 4, and 5

Without removing the catalyst after the degassing of test 2, the reactants are recharged three times in succession and 4 successive operations are thus carried out on the same catalyst charge (same temperature and same duration as in the case of Example 2).

|  | Test No. | | |
| --- | --- | --- | --- |
|  | 3 | 4 | 5 |
| $CCl_3CH_2Cl$ (g) | 43.2 | 42.7 | 43.8 |
| HF (g) | 41.3 | 41.3 | 41.9 |
| Weight of products obtained (g) | 28.9 | 29 | 29.5 |
| $CF_3CH_2Cl$ content | 99.6% | 99.5% | 99.1% |

The autoclave was weighed between each test and there was no increase in weight. After the last test the autoclave was opened and, as in Example 1, contained only a hygroscopic product consisting solely of antimony, titanium, and fluorine.

EXAMPLE 6

The following are charged onto a catalyst prepared, as in Example 2, from 5.7 g of $SbCl_3$, 5 g of $TiCl_4$ and HF:

44.3 g of $CCl_3CH_2Cl$
41.6 g of HF.

The reactor is heated to 110° C. over one and a half hours and is maintained at this temperature for 4 hours. The pressure has risen to 40.5 bars in this case. The analysis of the product recovered (31 g) makes it possible to calculate a degree of conversion of $CCl_3CH_2Cl$ of 71.8% into $CF_3CH_2Cl$ and of 24.5% into $CF_2ClCH_2Cl$.

By way of comparison, tests were carried out without catalyst and with titanium and trivalent antimony halides by themselves.

COMPARATIVE TEST 7

24 g of $CCl_3CH_2Cl$ and 36 g of HF were charged into the autoclave. After 5 hours', reaction at 150° C. the products recovered enabled the following balance to be established:

| $CCl_3CH_2Cl$ conversion: | 46% |
| --- | --- |
| Conversion of $CCl_3CH_2Cl$ | |
| into $CCl_2=CHCl$ | 17.6% |
| into $CFCl_2—CH_2Cl$ | 25.8% |
| into $CF_2Cl—CH_2Cl$ | 0.5% |

COMPARATIVE EXAMPLE 8

Titanium fluoride was prepared in the autoclave by reacting, as described in Example 2, 10.3 g of $TiCl_4$ (0.055 moles) and 20 g of HF (1 mole). 42 g of $CCl_3CH_2Cl$ (0.25 moles) and 52 g of HF (2.6 moles) were then introduced cold. The reaction mixture was then heated to 150° C. over 2 hours and maintained at this temperature for 3 and a half hours. After degassing, 26.5 g of product were recovered, containing 54.8% of $CF_3CH_2Cl$ and 38.4% of $CF_2ClCH_2Cl$.

In this case, the autoclave revealed a weight increase of 1.7 g, corresponding to 4% of the $CCl_3CH_2Cl$ employed and consisting essentially of polymerized products.

COMPARATIVE EXAMPLE 9

12 g of $SbCl_3$ (0.052 moles) and 20 g of HF (1 mole) were reacted as before. 43.7 g of $CCl_3CH_2Cl$ (0.26 moles) and 89 g of HF (4.45 moles) were then charged. After reaction in the same conditions as in Example 2, 32 g of product were recovered, its analysis making it possible to calculate the conversions of $CCl_3CH_2Cl$:

3.3% into $CF_3CH_2Cl$
79.4% into $CF_2ClCH_2Cl$
4.2% into $CFCl_2CH_2Cl$
3.2% into $CCl_2=CHCl$

EXAMPLE 10

A catalyst was prepared, as described in Example 2, from 11.4 g of $SbCl_3$ (0.05 moles), 9.4 g of $TiCl_4$ (0.05 moles) and 40 g of HF. After removal of the HF and HCl acids, 33.6 g of trichloroethylene (0.255 moles) and 80.7 g of HF (4.03 moles) were charged. The reaction mixture was heated to 150° C. over two hours and maintained at this temperature for 3 and a half hours. The pressure rose to 55 bars. After degassing, 29.5 g of product were recovered, containing 97.9% of $CF_3CH_2Cl$ and 2% of $CF_2ClCH_2Cl$, which corresponds to a 95.4% conversion of trichloroethylene into $CF_3CH_2Cl$.

EXAMPLE 11

The operation was carried out in the same conditions as in Example 10, but employing 4.8 g of $TiCl_4$ and 5.7 g of $SbCl_3$ and charging 34.9 g of trichloroethylene and 40.6 g of HF. After reaction at 150° C., the pressure stabilized at 41 bars and 31.5 g of product were collected, containing 10% of $CF_3CH_2Cl$ and 89% of $CF_2ClCH_2Cl$.

After degassing the autoclave, the increase in weight of the latter corresponded to 6.9 g, that is to say a weight very close to that of the catalyst.

EXAMPLE 12

34.9 g of trichloroethylene (0.265 moles), 41.4 g of HF (2.07 moles) and 12.6 g of HCl (0.34 moles) were charged into the autoclave containing the catalyst of Example 11. The reaction was then carried out at 150° C. as in the case of Example 11 and a pressure of 60 bars was reached. After degassing, 30.1 g of product were collected, containing 99.8% of $CF_3CH_2Cl$, that is a 95.5% conversion of trichloroethylene into $CF_3CH_2Cl$.

EXAMPLE 13

35 g of trichloroethylene and 82 g of HF were charged into the autoclave containing the catalyst employed for Example 10 and which had been obtained from 11.4 g of $SbCl_3$ and 9.4 g of $TiCl_4$. The autoclave was then heated to 110° C. over an hour and a half and maintained at this temperature for 4 hours. The pressure stabilized at 29 bars. After cooling and degassing, 32.3 g of product were recovered, containing 41.3% of $CF_3CH_2Cl$ and 51.9% of $CF_2ClCH_2Cl$.

EXAMPLE 14

34.9 g of trichloroethylene and 81.6 g of HF were charged into the autoclave containing the catalyst of Example 13. The reactor was heated to 130° C. over 2 hours and maintained at this temperature for 3 and a half hours. After cooling and degassing, 30.5 g of product were recovered, containing 76.7% of $CF_3CH_2Cl$ and 16.4% of $CF_2ClCH_2Cl$.

COMPARATIVE EXAMPLE 15

By forming $SbF_3$ in the autoclave by reacting 11.4 g of $SbCl_3$ and 20 g of HF and by then charging 35 g of trichloroethylene and 82.3 g of HF, the following results were obtained after reaction at 150° C. and 5 and a half hours:

| | |
|---|---|
| Unconverted $CCl_2=CHCl$ | 17% |
| Conversion into $CF_2ClCH_2Cl$ | 37.5% |
| Conversion into $CFCl_2CH_2Cl$ | 44.5% |
| Conversion into $CF_3CH_2Cl$ | 0.3% |

By carrying out the reaction in the presence of only $TiF_4$ (obtained from 9.5 g of $TiCl_4$ and 20 g of HF) and with 34.4 g of trichloroethylene and 40.7 g of HF, a very large quantity of polymers remaining in the reactor, corresponding to more than 40% of the trichloroethylene employed, was obtained after reaction at 150° C. The products recovered during the degassing corresponded, furthermore, to 14.6 g containing 69% of $CF_3CH_2Cl$ and 26% of $CF_2ClCH_2Cl$.

EXAMPLE 16

11.6 g of $SbCl_3$ (0.05 moles) and 8.8 g of $TiCl_4$ (0.046 moles) were charged into the autoclave. After cooling in liquid nitrogen, 101.1 g of $CCl_3CHCl_2$ (0.5 moles) and 81.2 g of HF (4.06 moles) were introduced. The mixture was then heated to 150° C. over 2 hours and maintained at this temperature for 3 and a half hours. After cooling and degassing, 81 g of product were recovered, containing:

| | |
|---|---|
| $CF_2=CCl_2$ | 6.3% |
| $C_2Cl_4$ | 4% |
| $CF_3CHCl_2$ | 1% |
| $CFCl_2CHCl_2$ | 3% |
| $CF_2ClCHCl_2$ | 82% |

EXAMPLE 17

The operation was carried out in the same conditions as in Example 10, but employing 4.75 g of $TiCl_4$ (0.025 mole) and 5.7 g of $SbCl_3$ (0.025 mole) and, after fluorination of the catalyst, charging 32.9 g of trichloroethylene (0.25 mole) and 80 g of HF (4 moles). The reaction mixture was heated to 150° C. over two hours and maintained at this temperature for 3 and a half hours. The pressure rose to 52 bars. After degassing, 29 g of product were recovered, containing 83% of $CF_3CH_2Cl$, 14% of $CF_2ClCH_2Cl$ and 2% of $CFCl_2CH_2Cl$.

EXAMPLE 18

By operating as in Example 17 with 3.57 g of $TiCl_4$ (0.0188 mole) and 7.12 g of $SbCl_3$ (0.031 mole), a product was recovered which contains 55% of $CF_3CH_2Cl$ and 44% of $CF_2ClCH_2Cl$.

EXAMPLE 19

By operating as in Example 17 with 7.12 g of $TiCl_4$ (0.0375 mole) and 2.85 g of $SbCl_3$ (0.0125 mole), a product was recovered containing 96% of $CF_3CH_2Cl$ and 3% of $CF_2ClCH_2Cl$.

EXAMPLE 20

By operating as in Example 17 with 8 g of $TiCl_4$ (0.042 mole) and 1.8 g of $SbCl_3$ (0.0078 mole), a product was recovered containing 99.6% of $CF_3CH_2Cl$.

EXAMPLE 21

A catalyst was prepared, as described in Example 2, from 3.6 g of $SbCl_3$ (0.016 mole), 16 g of $TiCl_4$ (0.085 mole) and 40 g of HF.

Then, 50.6 g of $CCl_3CHCl_2$ (0.25 mole) and 100 g of HF (5 moles) were charged. The reaction mixture was heated to 150° C. over two hours and maintained at this temperature for 3 and a half hours. The pressure rose to and stabilized at 54.5 bars.

After cooling and degassing, 38 g of product were recovered, containing 96.3% of $CF_2Cl$—$CHCl_2$ and 2.3% of $CF_3CHCl_2$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above mentioned references are hereby incorporated by reference.

We claim:

1. Process for liquid phase fluorination of a halogenated hydrocarbon using hydrofluoric acid comprising fluorinating a halogenated hydrocarbon by contacting the halogenated hydrocarbon with a reactant mixture consisting of hydrofluoric acid and a catalyst consisting of a mixture of an antimony trihalide and of a titanium tetrahalide wherein the antimony remains in the trivalent state.

2. Process according to claim 1, wherein the fluorination is carried out at a temperature between 40° and 180° C.

3. Process according to claim 1, wherein fluorination is carried out in an autoclave under autogenous pressure.

4. Process according to claim 1, wherein fluorination is carried out continuously at a pressure which is at least equal to that needed to keep the reaction mixture in liquid phase.

5. Process according to claim 1, wherein the molar ratio of the Sb+Ti catalyst to the compound to be fluorinated is between 0.1 and 0.6.

6. Process according to claim 1, in which the molar ratio HF/compound to be fluorinated is greater than 1.

7. Process according to claim 1, wherein the halogenated hydrocarbon to be fluorinated is a chlorinated derivative of ethane or of ethylene.

8. Process according to claim 5, wherein the molar ratio is between 0.2 and 0.4.

9. Process according to claim 6, wherein the molar ratio is between 5 and 20.

10. Process according to claim 1, wherein the molar proportion of antimony trihalide is between 10 and 70% and that of titanium tetrahalide between 90 and 30%.

11. Process according to claim 1, wherein the molar proportion of titanium tetrahalide is between 50 and 90%.

12. Process according to claim 1, consisting of a mixture of antimony trifluoride and of titanium tetrafluoride.

13. Process according to claim 1, wherein the catalyst is obtained by fluorination of a mixture of antimony trichloride and of titanium tetrachloride.

14. Process according to claim 1, wherein the fluorination of the mixture of chlorides is carried out at the same time as that of a halogenated hydrocarbon.

* * * * *